(12) United States Patent
Schulman et al.

(10) Patent No.: US 8,991,680 B1
(45) Date of Patent: Mar. 31, 2015

(54) METHOD OF MANUFACTURE OF AN ELECTRODE ARRAY

(75) Inventors: Joseph H. Schulman, Santa Clarita, CA (US); Guangqiang Jiang, Valencia, CA (US); Charles L. Byers, Canyon Country, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 698 days.

(21) Appl. No.: 13/211,233

(22) Filed: Aug. 16, 2011

Related U.S. Application Data

(63) Continuation-in-part of application No. 11/380,877, filed on Apr. 28, 2006, now Pat. No. 8,024,022.

(60) Provisional application No. 60/685,032, filed on May 25, 2005.

(51) Int. Cl.
 B23K 31/02 (2006.01)
 B23K 1/19 (2006.01)

(52) U.S. Cl.
 CPC ........................................ B23K 1/19 (2013.01)
 USPC ....................................... 228/180.1; 228/246

(58) Field of Classification Search
 None
 See application file for complete search history.

(56) References Cited

U.S. PATENT DOCUMENTS

| | | | |
|---|---|---|---|
| 3,453,478 A | | 7/1969 | Soulders et al. |
| 3,755,704 A | | 8/1973 | Spindt et al. |
| 3,789,471 A | | 2/1974 | Spindt et al. |
| 3,812,559 A | | 5/1974 | Spindt et al. |
| 3,834,015 A | * | 9/1974 | Di Renzo ........................ 29/843 |
| 4,180,700 A | * | 12/1979 | Kraska et al. ......... 174/152 GM |
| 4,350,886 A | * | 9/1982 | Pommerrenig ............... 250/239 |
| 4,361,720 A | * | 11/1982 | Resneau et al. .............. 174/16.3 |
| 4,774,760 A | * | 10/1988 | Seaman et al. .................. 29/840 |
| 4,837,049 A | | 6/1989 | Byers et al. |
| 4,842,184 A | * | 6/1989 | Miller, Jr. .................. 228/180.1 |
| 4,969,468 A | | 11/1990 | Byers et al. |
| 5,046,242 A | * | 9/1991 | Kuzma ............................ 29/878 |
| 5,145,104 A | * | 9/1992 | Apap et al. ................. 228/180.1 |

(Continued)

FOREIGN PATENT DOCUMENTS

| | | | |
|---|---|---|---|
| JP | 01-183084 A | * | 7/1989 |
| JP | 02-309581 A | * | 12/1990 |
| RU | 2100164 C1 | * | 12/1997 |

OTHER PUBLICATIONS

White, Robert L., "Integrated Circuits and Multiple Electrode Arrays," pp. 199-207, Proc. First International Conference on Electrical Stimulation of the Acoustic Nerve as a Treatment for Profound Sensorineural Deafness in Man, pub. By Velo-Bind, Inc. (1974), ed. By Michael M. Merzenich, et al.

(Continued)

*Primary Examiner* — Kiley Stoner
(74) *Attorney, Agent, or Firm* — Gary D. Schnittgrund

(57) ABSTRACT

The electrode array is a device for making electrical contacts with cellular tissue or organs. The electrode array includes an assembly of electrically conductive electrodes arising from a substrate where the electrodes are hermetically bonded to the substrate. A method of manufacture of an electrode array and associated circuitry is disclosed where the braze preform tab disappears during the braze bonding process and is completely drawn into the substrate feedthrough holes such that the braze perform tab is completely involved in the braze joint and is no longer connecting the adjacent electrodes.

3 Claims, 6 Drawing Sheets

(56) References Cited

U.S. PATENT DOCUMENTS

| | | | |
|---|---|---|---|
| 5,215,088 A | | 6/1993 | Normann et al. |
| 5,242,097 A | * | 9/1993 | Socha .......................... 228/56.3 |
| 5,626,278 A | * | 5/1997 | Tang ............................ 228/56.3 |
| 5,957,364 A | * | 9/1999 | Socha .......................... 228/56.3 |
| 6,179,631 B1 | * | 1/2001 | Downes et al. ................ 439/83 |
| 6,251,767 B1 | * | 6/2001 | Heinen ......................... 438/616 |
| 6,325,280 B1 | * | 12/2001 | Murphy ....................... 228/246 |
| 6,521,350 B2 | | 2/2003 | Fey et al. |
| 6,543,676 B2 | * | 4/2003 | Tung et al. ................... 228/215 |
| 6,817,092 B2 | * | 11/2004 | Custer et al. ................... 29/843 |
| 6,986,453 B2 | | 1/2006 | Schnittgrund |
| 6,989,200 B2 | | 1/2006 | Byers et al. |
| 2001/0041481 A1 | * | 11/2001 | Cachina et al. ............... 439/876 |
| 2004/0131318 A1 | * | 7/2004 | Mori et al. ...................... 385/92 |
| 2004/0232204 A1 | * | 11/2004 | Wolf ............................ 228/49.1 |
| 2009/0080140 A1 | * | 3/2009 | Iyer et al. ...................... 361/302 |

OTHER PUBLICATIONS

Wise, et al., "An Integrated Circuit Approach to Extracellular Microelectrodes,", IEEE Transactions on Biomedical Engineering, vol. BME-17(3), pp. 238-247, Jul. 1970.

Ko, "Solid State Physical Transducers for Biomedical Research", IEEE Transactions on Biomedical Engineering, vol BME-33, pp. 153-162, Feb. 1986.

Spindt, et al., "Physical Properties of Thin-Film Field Emission Cathodes with Molybdenum Cones," J. App. Phys., vol. 47 (12) Dec. 1976.

Wise, et al., "A Low-Capacitance Multielectrode Probe for Use in Extracellular Neurophysiology", IEEE Transactions on Biomedical Engineering, vol. BME-22(3), May 1975.

* cited by examiner

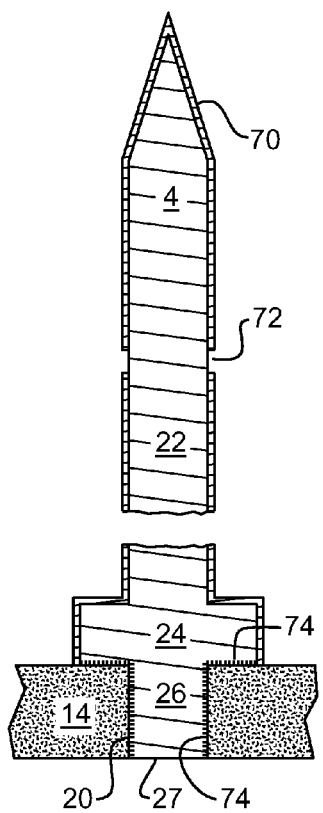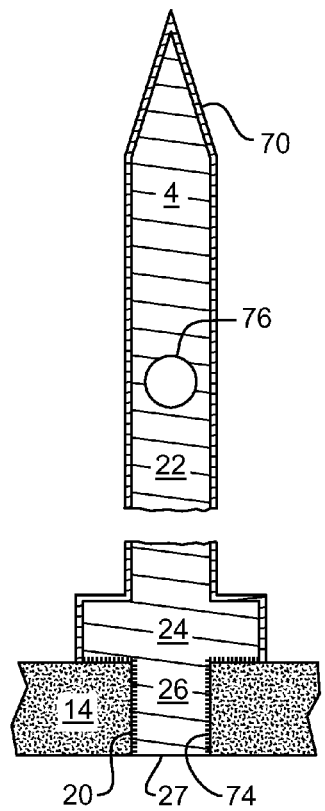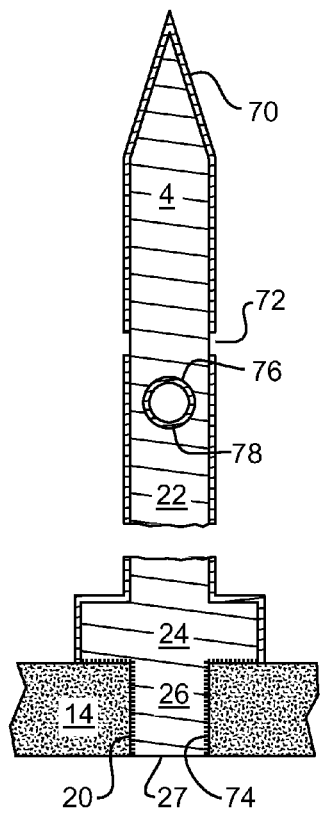
*Fig. 7*
*Fig. 8*
*Fig. 9*

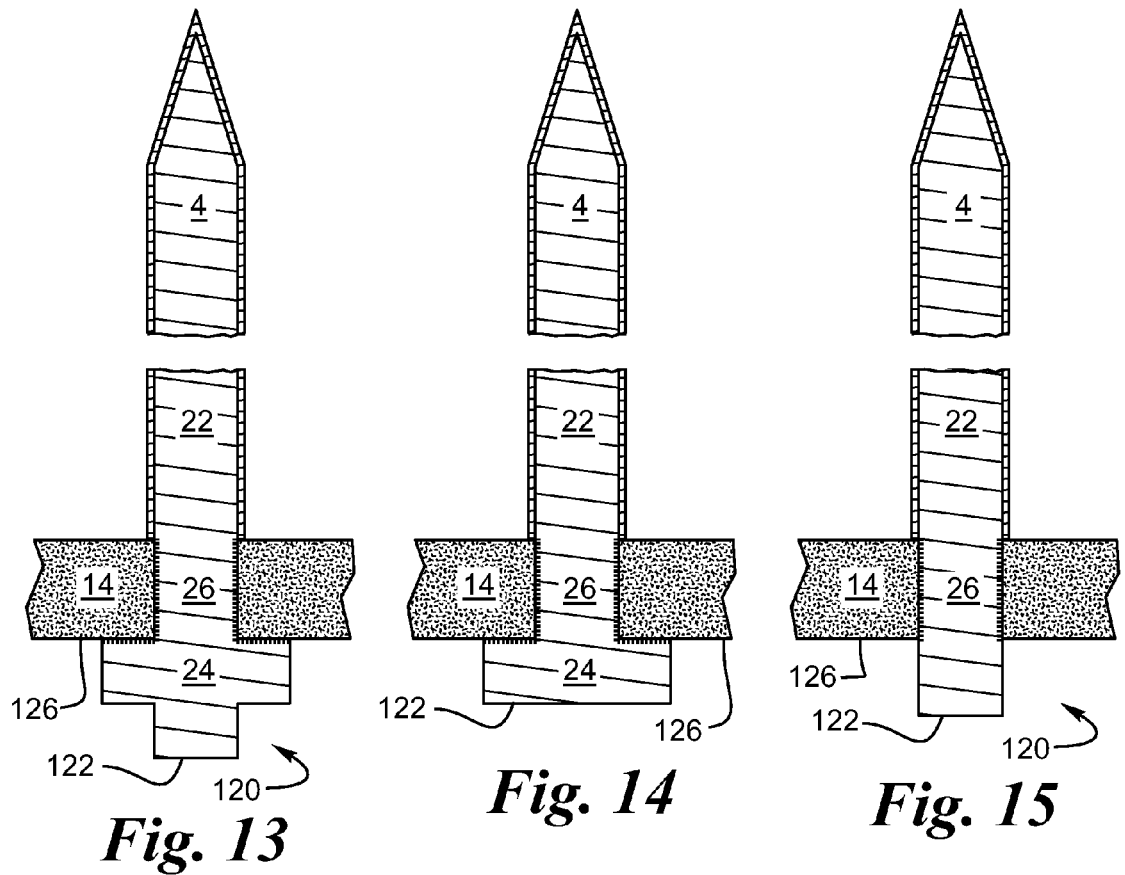
*Fig. 13*  *Fig. 14*  *Fig. 15*
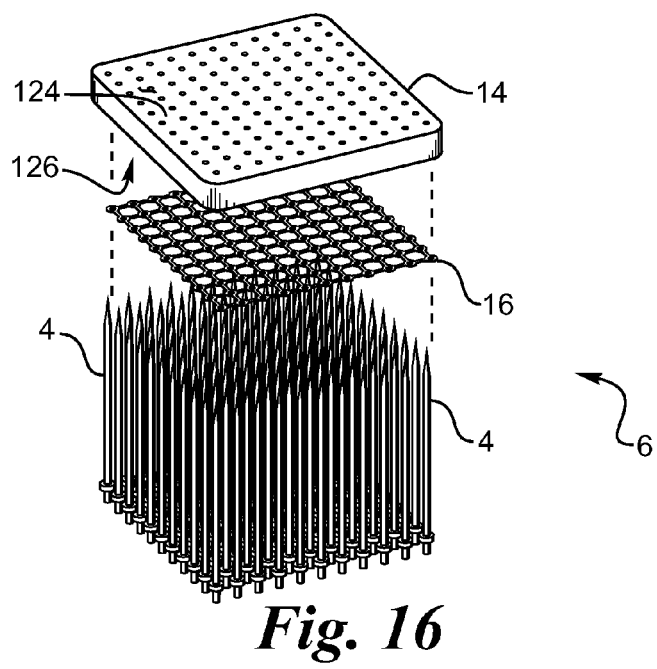
*Fig. 16*

METHOD OF MANUFACTURE OF AN ELECTRODE ARRAY

CROSS REFERENCE TO RELATED APPLICATIONS

This application is a continuation in part of U.S. application Ser. No. 11/380,877, filed on Apr. 28, 2006, now U.S. Pat. No. 8,024,022 issued on Sep. 20, 2011, which claims priority from U.S. provisional application Ser. No. 60/685,032 filed on May 25, 2005; both of which are incorporated herein by reference.

BACKGROUND OF THE INVENTION

1. Field of the Invention

This invention relates to a hermetically sealed three-dimensional electrode device and a method of manufacturing such a device. The device may be particularly useful for neuron interface and more specifically as a cortical implant.

2. Description of Related Art

Including Information Disclosed Under 37 CFR 1.97 and 1.98

A nerve is a cordlike structure which is composed of numerous nerve fibers conveying impulses between a part of the central nervous system and some other region of the body. A nerve is made up of individual nerve fibers with their sheaths and supporting cells, small blood vessels, and a surrounding connective tissue sheath. Each nerve fiber is surrounded by a cellular sheath (neurilemma) from which it may or may not be separated by a laminated lipo-protein layer (myelin sheath). A group of such nerve fibers surrounded by a sheet of connective tissue (perineurium) is called a fasciculus. The fasciculi are then bound together by a thick layer of connective tissue (epineurium) to form the nerve.

Neurologists have long sought an electrode device which could establish stable electrical contact with a large number of individual nerve fibers within a nerve or a large number of individual neurons. Such a device would find wide medical application for sensing neurological impulses, facilitating the analysis and interpretation of such impulses, and delivering electrical stimuli to target nerve fibers as a reaction to such analysis or as a result of external input. The ideal electrode device would be adapted to the anatomy of the nerve so that it could penetrate the nerve in a nondestructive fashion in order to form focused electrical contacts with a very large number of individual nerve fibers.

Nerve cuff electrodes are employed in the neurological sciences for sensing nervous impulses and for electrically stimulating nerves. The nerve cuff electrode encircles the entire nerve and senses gross nervous impulses arising from the nerve fibers within the nerve. The nerve cuff electrode may also be employed to electrically stimulate the nerve. Individual nerve fibers within a nerve may be functionally distinct from the other nerve fibers. The utility of the nerve cuff electrode is limited by its inability to specifically direct signals to or from selected nerve fibers within the nerve.

In order to make electrical contact with individual nerve fibers within a nerve, narrow gauge needle electrodes may be employed. When a narrow gauge needle is inserted into the nerve, there is a chance that it may make electrical contact with an individual nerve fiber or a small number of such fibers. If electrical contact is desired with each of several nerve fibers, then several needle electrodes must be employed. However, the technique of using multiple needle electrodes becomes progressively more and more difficult as the number of electrodes increases. Hence, there is a limit to the number of needle electrodes which can be usefully employed on a single nerve. Also, the electrical contact between a needle electrode and its corresponding nerve fiber can be disrupted by muscle motion and other forms of motion, since the end of the needle opposite the electrode extends outside the nerve and can be levered by relative motion of neighboring tissues. Therefore, long term implantation of needle electrodes with stable electrical contact with nerve fibers is not possible with prior art needle electrodes.

An electrode array having several electrodes integrated into one device is disclosed by Robert L. White. (Proc. First International Conference on Electrical Stimulation of the Acoustic Nerve as a Treatment for Profound Sensorineural Deafness in Man, pub. by Velo-Bind, Inc. (1974), ed. by Michael M. Merzenich, et al., entitled "Integrated Circuits and Multiple Electrode Arrays," pp 199-207, by Robert L. White). White's electrode array employs a prong shaped base fabricated from a silicon wafer. The silicon base supports an array of electrodes which are deposited thereon toward the end of the prong. Each of the electrodes is small, flat, and circular, about 50 micrometers in diameter. Each electrode is connected to a corresponding conductor which carries signals to and from the electrode. The conductor is electrically insulated from the tissue by a layer of silicon dioxide. In use, the prong is inserted tip first into neural tissue. Neural tissue is displaced by the prong as it is inserted. Substantial damage to neural tissue can result from the insertion process due to the relatively large bulk of the prong. Since neural tissue slides tangentially past the electrodes during the insertion process, the flatness of the electrodes helps to minimize the resultant disruption and destruction of neural tissue. Once the device is inserted, the flatness of the electrodes limits the contact between the electrode and the neural tissue. Flat electrodes can make electrical contact only with neural tissue which is directly adjacent to the surface of the prong.

Multiple electrode devices with microelectrode tips protruding beyond and in a plane parallel to a silicon carrier (i.e. planar electrodes) are disclosed by Wise, et al. (IEEE Transactions on Biomedical Engineering, vol. BME-17(3), pp 238-247, July 1970, "An Integrated Circuit Approach to Extracellular Microelectrodes," and vol. BME-22(3), May 1975, "A Low-Capacitance Multielectrode Probe for Use in Extracellular Neurophysiology") and by Ko (IEEE Transactions on Biomedical Engineering, vol. BME-33, pp 153-162, February 1986, "Solid State Physical Transducers for Biomedical Research"). Wise teaches that the lateral spacing and length of the protruding tips may be controlled to produce various planar electrode arrays. Like the White device, the silicon carrier of the Wise and Ko devices have the shape of a prong and may cause significant tissue damage to the nerve during the insertion process. Also, if the Wise and Ko prong-shaped devices are implanted, their large bulk compromises the stability of the electrical contact between the electrode tips and individual target cells. Additionally, the thinness of the prong can make it susceptible to shear damage with side loading. Further, since the silicon carrier and the electrode tips are essentially coplanar with the tips cantilevered freely beyond the end of the carrier, the carrier imparts little if any transverse stability to the fragile tips during insertion of the Wise, et al. and Ko prong-shaped devices or after their implantation. Moreover, the number of useful electrodes which may be incorporated into the Wise and Ko devices is inherently limited. Since the electrode tips are aligned in a row along the edge of the silicon carrier, it is not possible to array the electrodes into a configuration with more than one dimension.

Known "bed of nails" devices are disclosed by Byers, et al. in U.S. Pat. No. 4,837,049, issued Jun. 8, 1989, and U.S. Pat.

No. 4,969,468, issued Nov. 13, 1990, and by Normann, et al. in U.S. Pat. No. 5,215,088, issued Jun. 1, 1993, all of which are incorporated herein by reference. These inventions relate to electrodes for electrically sensing or stimulating living tissues. In particular, the invention relates to electrode arrays and to methods for making and using such arrays. The tips of the needles may be left exposed by a dielectric coating. Below the needle is a metallic layer upon which the conductors are formed. The dielectric may be silicon dioxide. However, these devices are difficult to seal "hermetically", as is required when they are part of a "smart" array containing electronic signal processing means.

The needles may be constructed as "cones" and a method of construction may use techniques similar to those taught in U.S. Pat. Nos. 3,755,704, 3,789,471, and 3,812,559, each naming Charles A. Spindt, et al. as inventors U.S. Pat. No. 3,453,478, naming Kenneth R Soulders and Louis N. Heynick as inventors, also discloses background technology for constructing cones. Further disclosure on known fabrication technology may be found in an article by C. A. Spindt, et al., entitled "Physical Properties of Thin-Film Field Emission Cathodes with Molybdenum Cones," J. App. Phys., vol. 47 (12) December 1976.

Evaporating metal to form the needles of platinum, activated iridium, platinum-iridium alloy, rhenium, or other suitable implantable electrode material is presented.

Thus, what is missing and what is needed by practicing neurologists is an implantable electrode device which can electrically contact a large number of individual cells within an organ or tissue for sensing and/or controlling various bodily functions. The individual contacts should each be focused within a small region so that they involve single cells. However, the range of the contacts should extend over a relatively large region within the organ or tissue. The electrodes of the device should make positive contact with target cells, be firmly anchored, and should be stable over long periods of time, even with recurrent movement in adjacent tissues. On the other hand, the device should penetrate the target organ without being intrusive so that tissue damage to the target organ is minimal. The device should have a small volume and a robust construction for practical medical applications.

BRIEF SUMMARY OF THE INVENTION

A method for making an electrically conductive electrode array comprising the steps of obtaining a substrate with at least two feedthroughs; inserting a braze perform having a melting point that is comprised of tabs which locate holes, said holes accept an electrically conductive electrode, and voids that are defined by said tabs on said substrate; inserting said electrically conductive electrode into each of said at least two feedthroughs; and bonding said electrically conductive electrode to each of said at least two feedthroughs by a brazing process at a known temperature wherein the tab is drawn into the braze joint.

Other objects and features will be apparent from the following description together with the drawings.

BRIEF DESCRIPTION OF THE SEVERAL VIEWS OF THE DRAWINGS

FIG. 7 presents a cross-sectional view of a coated electrode with a revealed conductive band.

FIG. 8 presents a cross sectional view of a coated electrode with a conductive through-hole.

FIG. 9 presents a cross-sectional view of a coated electrode with a coated through-hole and a revealed conductive band.

FIG. 13 is a cross-sectional view of a coated electrode that has been inserted through the bottom surface of the substrate.

FIG. 14 is a cross-sectional view of a coated electrode that has been inserted through the bottom surface of the substrate.

FIG. 15 is a cross-sectional view of a coated electrode that is inserted through the bottom surface of the substrate.

FIG. 16 is an exploded view of the electrode array, braze preform, and substrate, where the electrode is inserted from the bottom surface of the substrate.

DETAILED DESCRIPTION OF THE INVENTION

Figure 1:
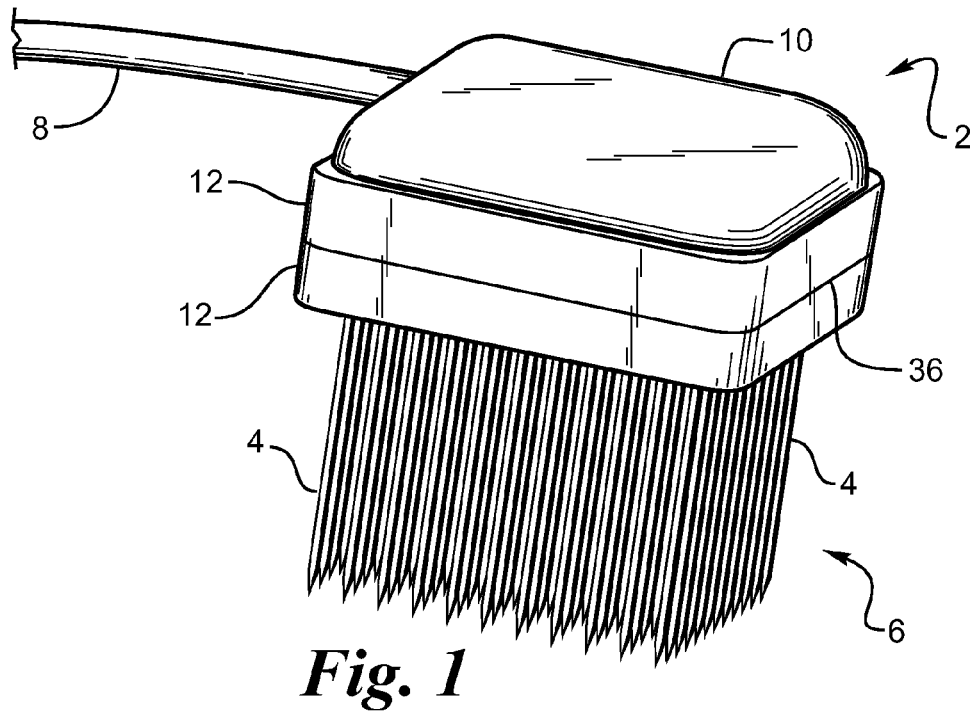
FIG. 1 is a perspective view of one embodiment of the electrode array illustrating an array of sharp electrodes arising from the substrate, a cable, and header. The array of sharp needles illustrates the concept of "bed-of-nails."

The invention is a method of manufacturing an electrode array 6, shown in FIG. 1, also known as a "bed-of-nails", which is applied to living tissue to provide an effective electrical connection therewith, whether for sensing or stimulating purposes. The electrode array 6 provides a multiple possibility of successful electrical contact, and causes minimal damage or upset to either the living tissue or to the body system. The electrode array 6 includes an arrangement of electrically conductive needles that arise from a substrate 14, are substantially normal thereto, and which serve as electrodes 4 (FIG. 2) for sensing or stimulation of living tissue. Terminals and electrical conductors may be employed to connect individual electrodes 4 or groups of electrodes of the electrode array 6 to other electrical circuits.

The bed-of-nails package 2 consists of the electrodes 4, which form an array 6 that may be in a planar, square or rectangular arrangement having regular spacing intervals, as depicted in the various embodiments presented in FIGS. 1 to 9 and 13 to 16, or which may be in an irregular or non-repetitive arrangement such as may be dictated by the desired function of the package 2. While the package 2 is presented as a generally rectangular package having rounded edges and corners, it may advantageously have a flat circular or ovaloid shape or other shape without limitation to those shapes just disclosed. The package 2 may have a thickness of about 2 mm, plus the length of the electrodes. In a preferred embodiment, the electrodes 4 are about 0.5 to 4.0 mm (0.02 to 0.16 inches) in length and about 0.02 to 0.10 mm (0.001 to 0.004 inches) in diameter. Aspect ratios (height to diameter) of 40:1 are readily achievable. In the embodiment presented, the electrode array 6 contains about 121 electrodes 4 in a square matrix. The electrodes 4 may, of course, be taller and narrower. Electrode spacing in the array may vary, as may the size of the needles. Of course, such electrodes 4 may be conical or other elongated shapes. The spacing of the electrodes 4, transversely across a nerve, would be from approximately 0.5 micrometer to on the order of 100 micrometers. "On the order of" means within the range of 0.1 to 10 times the dimension, in this context and as used herein. Spacing of the electrodes 4 along the length of a nerve might well be greater than the lateral spacing of the electrodes 4 across the nerve. That is, the spacing distance between electrodes 4 along the length of a nerve can vary a great deal. Electrodes 4 or electrode array 6 might well be longitudinally spaced 1,000 micrometers, 2,000 micrometers, etc., from one another, depending on the desired density of electrical contact with the nerve. The package 2 may be planar or may be alternately shaped to conform to a specific desired application, although only planar arrays are presented in FIGS. 1 to 9 and 13 to 16. The electrodes 4 material is biocompatible and is not limited to but may be selected from titanium, titanium alloy, platinum, platinum alloy, activated iridium, platinum-iridium alloy, conductive polymer, carbon or other suitable electrically conductive material known by those skilled in the art as suitable for use in connection with the body. In general, metals or other conductive substances which are inert and are least subject to corrosion are selected. In the case of stimulating devices, conductive materials which can handle the necessary current densities are required. In a preferred embodiment, the electrodes 4 are comprised of an electrically conductive and biocompatible material which may be elemental metals or alloys, such as but not limited to a titanium alloy, such as Ti-6Al-4V, Ti-5Al-2.5Fe, Ti-6Al-2Sn-4Zr-2Mo, Ti-6Al-6V-2Sn, or Ti-4Al-4Mo-2Sn—Si, or a platinum alloy, such as 90Pt-10Ir or 80Pt-20Ir, or pure platinum, or pure iridium. As will be discussed herein, coatings may be employed to enhance the stability of the electrodes 4. Candidate coating materials include, but are not limited to, gold, platinum, iridium, platinum oxide or iridium oxide, or another coating that is suitable for electrode application. The coating is applied to the electrodes 4 surface at least where the electrodes 4 are exposed to living tissue, as it is at a reveal 72 or at an uncoated through-hole 76.

The electrodes 4 must, therefore, be spaced according to the specific application. The electrodes 4 should be small and of the correct sharpness to avoid damaging the nerve. Also the electrically conductive portion of each electrode 4 should be small enough to contact only a single fiber and thereby obtain signals from only one fiber. Consequently, a preferred embodiment of the invention is to insulate the electrode, except at selected location or locations between a distal end 80 and a proximal end 82 of the electrodes 4, so that at least one electrically conductive portion of each electrode 4 is exposed. In this way, each electrode 4 may be designed to contact the living tissue at one location or at multiple locations, if more than one electrically conductive portion of the electrodes 4 are exposed to effect electrical contact more than one fiber of living tissue.

In addition, the electrodes 4 must be high or long enough to assure sufficient penetration of the desired nerve so as to make electrical connection with the nerve fiber inside the nerve. In order to reach the nerve fiber, the sheath and other connective tissues must be penetrated. However, "electrical connection" or "contact" with a nerve fiber or other body tissue may mean actual physical contact with the nerve fiber or tissue or it may mean being in sufficiently close location to sense the electrical signals therefrom or to stimulate the fiber or tissue.

The electrodes 4 spacing and length may vary on a given substrate 14. In order to reach down into a fissure in the brain, for example, it may be desirable to have longer electrodes 4 on one portion of the electrode array 6 and shorter electrodes 4 on another portion. Also, spacing density on one portion of the electrode array 6 may be greater or lesser than on another portion. The term "electrode array" as used herein means a collection of electrodes and includes systematic and orderly groupings or arrangements as well as including non-linear and irregular groupings or arrangements, which may be dictated by the function to be served by the electrode array. There may be an abrupt change of electrodes length or density, or both, in one or more directions. There may be graded or gradual changes in one or more directions.

It is to be understood that the array 6 may be sized to fit the particular application and may be planar, multiplanar, curved, twisted, or other desired shape as required in the particular circumstances involved. Ordinarily, the electrode array 6 is disposed on a rigid substrate 14. However, it is to be appreciated that the substrate 14 may be flexible, or that the electrode array 6 may be comprised of electrodes 4 on a plurality of substrates 14. In general, the electrodes 4 in an array 6 should be held in relatively fixed spacing with respect to each other. It is intended to cover by "relatively fixed" terminology, instances in which the substrate 14 is flexible, curved, stretchable, etc.

Among the suitable substrates 14 are, without limitation, ceramics, such as zirconia, more specifically stabilized-zirconia, partially-stabilized zirconia, tetragonal zirconia polycrystal, magnesia-stabilized zirconia, ceria-stabilized zirconia, yttria-stabilized zirconia, and calcia-stabilized zirconia, as well as silicon, sapphire, alumina, or germanium. Biomedical grade plastics may also be used such as the polyamides, polyimides, polymethacrylates, acrylics, polycarbonates, etc., to the extent that such plastics may be implantable or rendered implantable. These plastics cannot form a braze bond and, more importantly, they do not form a hermetic device.

The electrodes 4 may be arranged in random fashion or ordered in columns and/or rows or other ordered arrangements. The optimum embodiment from the standpoint of orderly electrical connection is an ordered arrangement. One embodiment which may be desired is that in which each electrode 4 (except, of course, those near the edges of the array 6) is surrounded by six other electrodes 4, all equidistantly spaced. The electrodes 4 are electrically connected to a terminal which may, likewise, be randomly located or located in orderly columns and/or rows. The terminal may include bonding pads which provide an electrical connection between the electrodes 4 and other electrical circuits. Connection points need not be in the same arrangement as the electrodes 4. Thus, the electrodes 4 may be located in columns, but not rows, and the terminals may be located in columns and rows.

In addition, the package 2 is comprised of a case 12 that may have two halves, as illustrated in FIG. 1. The two halves of case 12 are welded together at weld 36 to form a hermetic seal. The case is comprised of biocompatible materials, which in a preferred embodiment may be titanium or an alloy of titanium that is weldable.

Cable 8 transmits electrical signals to and/or from the package 2 and is electrically connected to the electrodes 4 in a manner to assure that the desired function of the device is achieved. Header 10 electrically isolates the connections between the cable 8 and the electrodes 4. The isolation formed by the header 10 is not necessarily hermetic and may therefore be accomplished by forming header 10 of an epoxy material or a biocompatible electrically insulating material, which need not form a hermetic seal in the instant application, but which provide electrical isolation between the feedthrough pins 34. In a preferred application, the number of electrical conductors in cable 8 approximate the number of feedthrough pins 34.

A cross-section of the device 2 is presented (FIG. 2) showing the electrodes 4 in a flat, rectangular electrode array 6, where each electrode 4 is hermetically bonded to substrate 14. Electronic components 18 are presented and consist of integrated circuit chips, capacitors, and other electronic components that are known to those skilled in the art. Inclusion of signal processing as part of the device enables a "smart" array, wherein it is necessary to have hermetic and biocompatible packaging for the bed of nails and electronics. The case 12 covers and encloses electronic components 18 and forms a hermetic seal with substrate 14 by, for example, a braze joint 86. Feedthrough pins 34 are shown in a preferred embodiment as flat headed pins that are comprised of a conductive brazeable metal, such as titanium or its alloys, niobium or its alloys, platinum or its alloys, iridium or its alloys, or silver or its alloys. The feedthrough pins 34 are bonded by known processes, such as brazing or welding, to the electrical conductors in cable 8.

Figure 2:
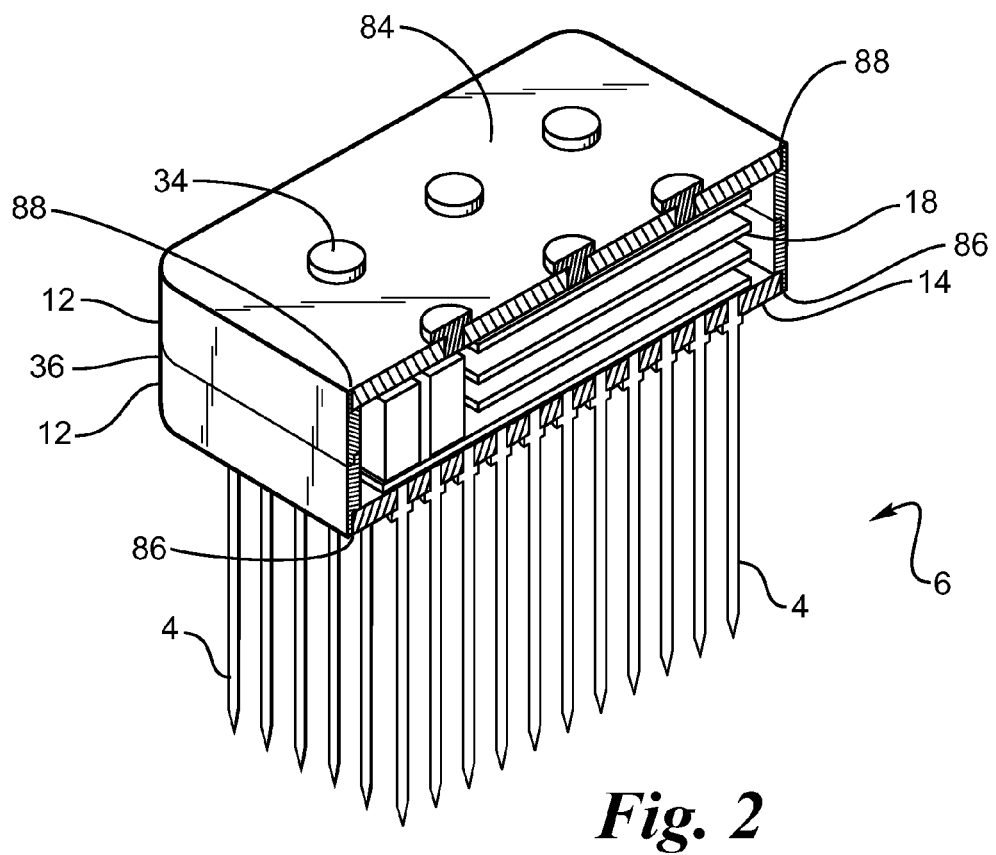
FIG. 2 is a cut-away of the perspective view of FIG. 1 illustrating the sharp electrodes passing through the substrate.

The embodiment of device 2 presented in FIG. 2 presents a preferred embodiment where a lid 84 is comprised of a material such as those candidates presented for substrate 14, notably zirconia or alumina. The lid 84 is attached by braze joint 88 to case 12, thereby forming a hermetic seal that protects electronics components 18. In alternate embodiments lid 84 may be comprised of a metal and may be comprised of the same material as case 12, potentially being an integral part of the assembly and thus avoiding joint 88.

Figure 3:
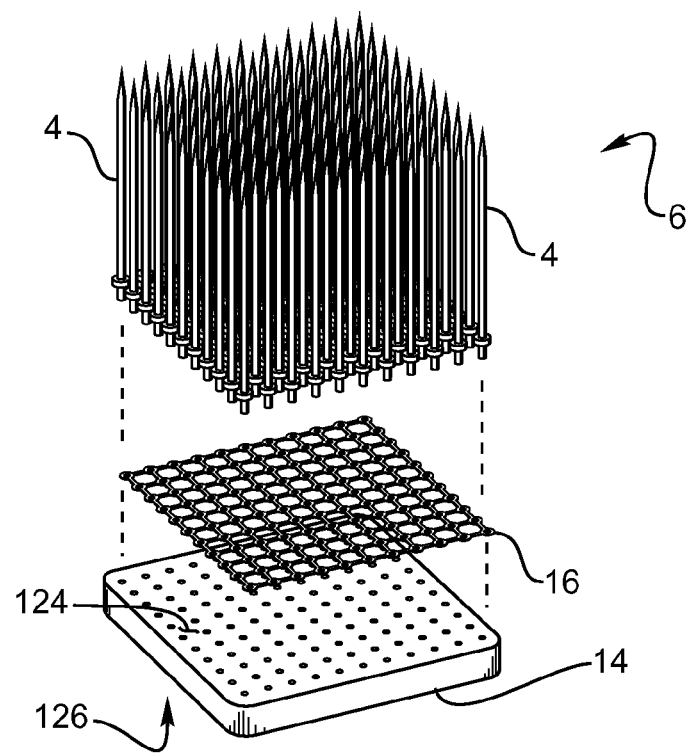
FIG. 3 presents an exploded view of the electrode array, braze preform, and substrate.

A sub-assembly to aid in describing the assembly process is presented in FIG. 3. In this embodiment the electrodes 4, while forming an electrode array 6, are inserted into a conforming braze preform 16, which is comprised of a braze material, from the top surface 124 of substrate 14. Substrate 14 receives a portion of each electrode 4 prior to being thermally processed to develop a hermetic seal between each electrode 4 and the substrate 14.

Figure 4:
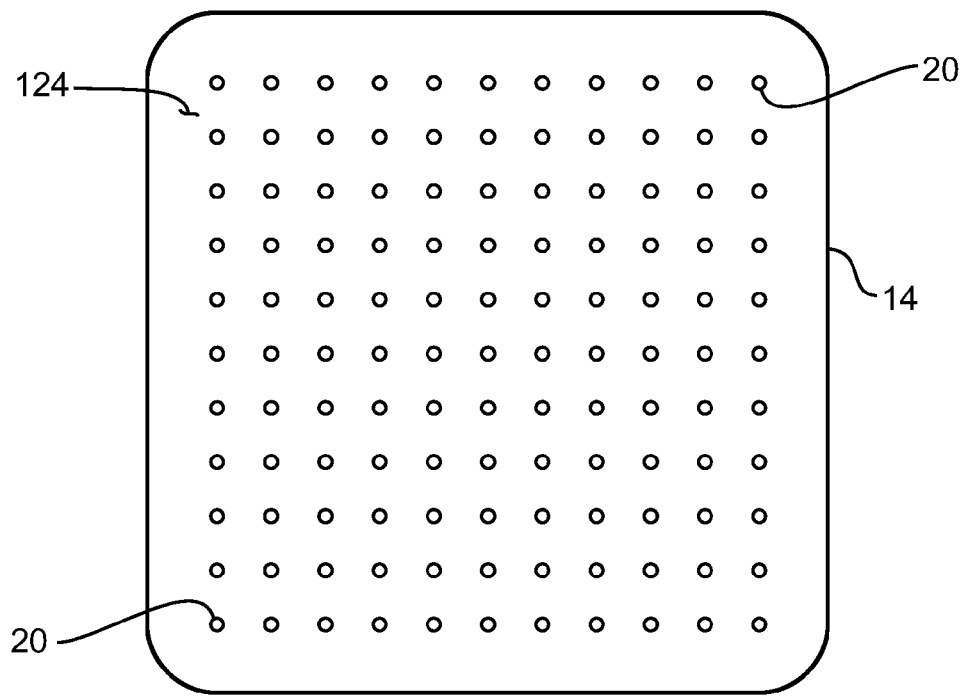
FIG. 4 is a top view of the substrate.
Figure 5:
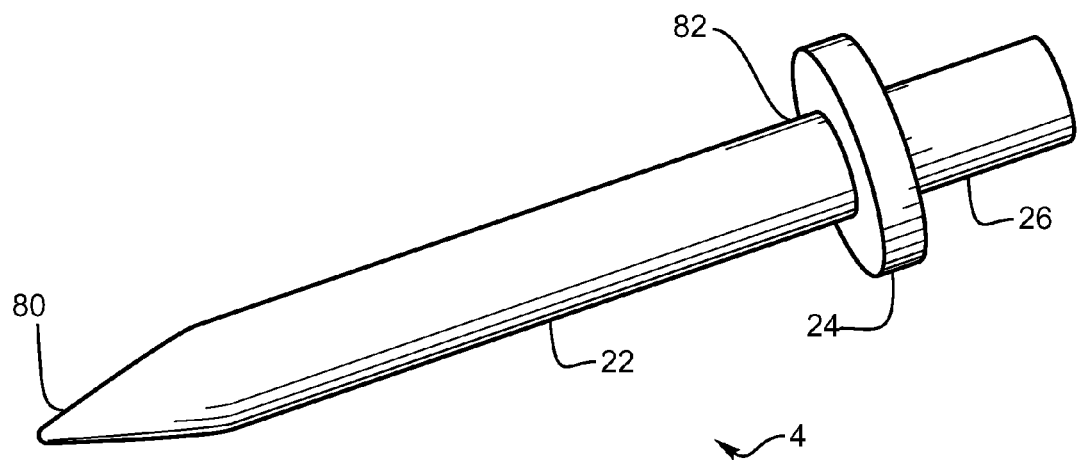
FIG. 5 is a perspective view of an electrode.

The substrate 14, FIG. 4, contains a number of feedthrough holes 20 which correspond to the number and configuration of electrodes 4 when they are arranged in the electrode array 6. The electrodes 4, as presented in FIG. 5, consists of a shaft 22 which has a sharp end at the distal end 80, for tissue penetration during use, and an end that contacts brazing head 24 at the proximal end 82. The electrode then terminates with feedthrough 26 which, in the embodiment presented in FIG. 5, enters feedthrough hole 20 from the top surface 124 until brazing head 24 contacts braze preform 16, which in turn contacts substrate 14. A feedthrough 26 is comprised of a hole 20, braze joint 74, and electrode. Substrate 14 is preferably comprised of a ceramic, preferably zirconia.

Figure 6:
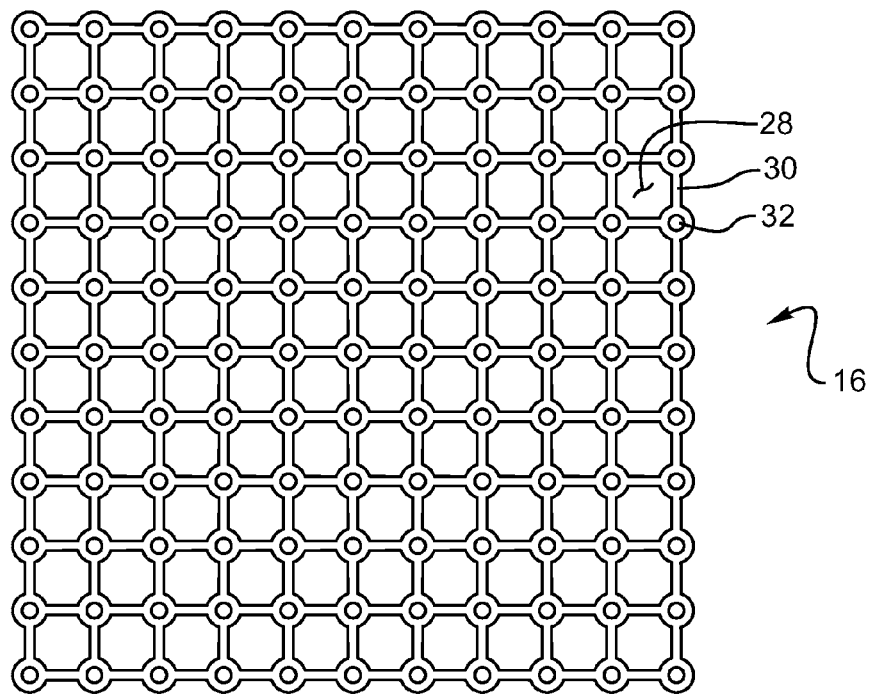
FIG. 6 is a top view of the braze preform.

Braze preform 16 is presented in FIG. 6 and is configured to have a hole 32 that corresponds to each substrate feedthrough hole 20, which in turn corresponds in approximate diameter and location to the electrodes 4 and electrode array 6. The braze material of braze preform 16 forms a plurality of tabs 30 thereby forming a matrix of braze material as a layer or multiple layers of braze material which, when thermally processed, hermetically bonds the electrodes 4 to the substrate 14. A large non-functional opening or void 28 is formed by the interconnecting tabs 30 and holes 32. The tabs 30 may be removed after brazing by sandblasting, dicing, laser ablation, etc. so that individual electrodes are isolated from each other.

However, in a preferred embodiment, the dimensions of braze preform is designed so that the tabs 30 will disappear after brazing due to surface tension as the melted preform tabs 30 are drawn into the braze joint 74 between the electrodes 4 and the substrate 14. In the case of using titanium or titanium alloys as the electrodes 4 material, a nickel braze preform 16 is preferred. During brazing, the tabs 30 on the braze preform 16 liquefy when some titanium (from the titanium electrodes 4) diffuses in and are pulled towards the electrode mating area due to surface tension. After brazing, the tabs 30 disappear. Titanium nickel layered laminates are the preferred braze material when electrodes 4 are comprised of noble metals. During brazing, the tabs 30 liquefy when its temperature reaches above its melting point and are pulled towards the electrode mating area due to surface tension. After brazing, the tabs 30 disappear. This is a preferred phenomenon as the braze perform 16 makes the assembly process much easier and the disappearing tabs 30 enable the electrodes 4 to remain insulated from each other.

It has been determined that the tabs have a maximum width of 0.1 inch, a maximum length of 0.2 inch, and a maximum thickness of 0.01 inch. Bonding of electrodes 4 into substrate feedthrough holes 20 has been determined to occur between 25 and 300 degrees Centigrade above the braze preform melting point.

Alternate embodiments of the braze preform 16 are conceived where the tabs 30 are removed and only a "braze washer" of material remains. Yet another embodiment of the braze preform 16 is a sheet of braze material that contains holes that accept the electrodes 4 in alignment with substrate feedthrough holes 20. The metal braze material may be, without limitation, an alloy, a composite, or a layered laminate that forms the desired thermally processed structure and is preferably comprised of nickel or an alloy of nickel, as disclosed in U.S. Pat. No. 6,521,350 issued to Fey, et al. on Feb. 18, 2003, which is incorporated by reference in its entirety. Also, U.S. Pat. No. 6,989,200, issued to Byers, et al. on Jan. 24, 2006; U.S. Pat. No. 7,022,4215 issued to Schnittgrund on Apr. 4, 2006; and U.S. patent application Ser. No. 10/793,006 filed by Schnittgrund on Mar. 3, 2004, now abandoned, all of which are incorporated by reference in their entirety, disclose candidate braze materials.

The cross-sectional view of electrodes 4 presented in FIG. 7 presents the shaft 22 in relation to the brazing head 24, which abuts substrate 14 and is attached thereto by braze material at a braze joint 74. The braze joint 74 continues along the interface formed between electrode feedthrough 26 and feedthrough hole 20. The proximal end of the electrodes 4 comprises a contact surface 27 for connection to other electrical circuits. The electrodes 4 are covered by electrically insulating coating 70 thereby preventing electrical contact with the tissue in which the electrodes 4 are placed, except at the electrically conductive reveal 72, which in a preferred embodiment is presented as an uncoated band that circumscribes shaft 22. More than one reveal 72 may placed on a given electrode 4 to enable monitoring several neural fibers, for example. Each fiber will have its own individual signal, which may be monitored individually by selecting the signal and utilizing electronic filtering to distinguish the several signals from each other. It is conceived that the distal tip 80 (FIG. 5) may be revealed also. The utilization of multiple reveals is most useful when electrical signals are being sensed, since in a stimulation mode, each reveal would stimulate each contact point simultaneously, while in the detection mode, the electronic package can discriminate between individual sensed inputs on a single electrode 4 having multiple reveals 72 or holes 76.

Coating 70 is comprised of a biocompatible and electrically insulating coating, such as parylene, polyimide, alumina, or zirconia. Coating 70 is preferably comprised of parylene, a well known organic coating that is biocompatible. Electrically conductive contact between tissue and electrodes 4 is limited by the position, size, and shape of the reveal 72.

An alternative embodiment of the electrodes 4 is presented in FIG. 8, wherein the electrodes 4 are coated with insulating coating 70 except at through-hole 76, which in this embodiment passes completely through the shaft 22. The inside of hole 76 is left uncoated, where electrically conductive contact with the tissue occurs.

A further feature of the embodiment presented in FIG. 8 is that the living tissue, which may be a nerve bundle or an axon, grows into the hole 76 and thereby anchors the electrode in position in the tissue. Hole 76 need not pass completely through shaft 22 to provide an anchor for the ingrowth of tissue. The hole 76 has a diameter of about 0.01 to 0.03 mm (0.0005 to 0.001 inches) and may be fabricated by laser drilling.

Another alternative embodiment is presented in FIG. 9, where the hole 76 is electrically insulated and coated along its inside walls with coating 78, which is preferably the same coating as the coating 70 on the outside of electrodes 4. In this embodiment the hole 76 provides an anchor to the living tissue. The reveal 72 provides electrical communication with the tissue.

Figure 10:
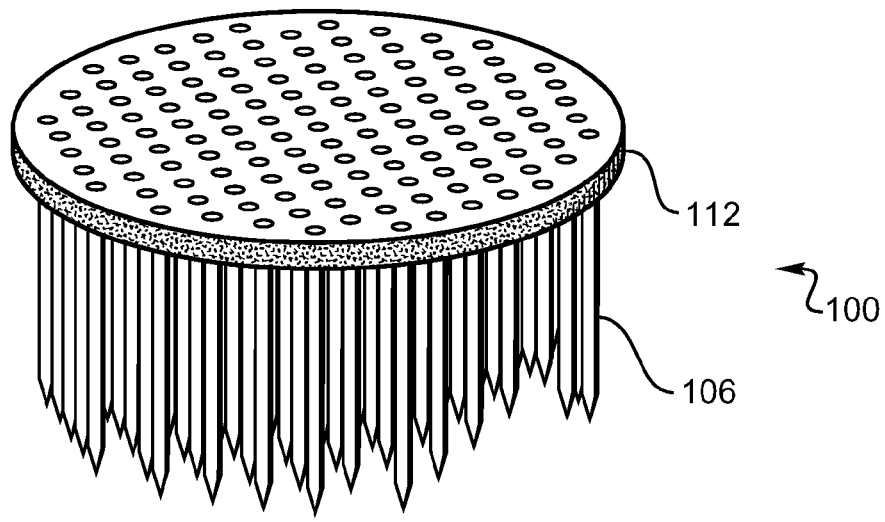
FIG. 10 is a perspective view of an embodiment of an electrode array illustrating an oval arrangement of irregular length electrodes.

A further embodiment of an electrode array 100 is presented in FIG. 10 wherein the electrodes 106, which are bonded to oval substrate 112, have variable lengths. The substrate 112 and electrode array 100 pattern may be oval, circular, rectangular, or an irregular shape without limitation. The reveals, not illustrated, may be located in one plane, at variable locations, or in a non-repeating pattern.

Figure 11:
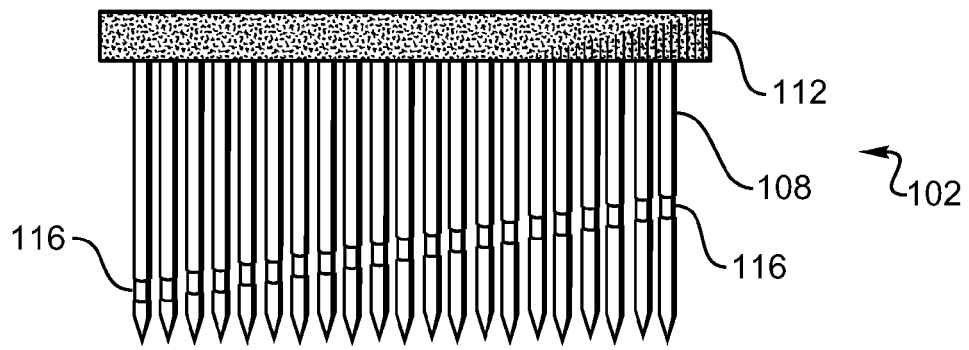
FIG. 11 is a side view of an embodiment of an electrode array illustrating equal length electrodes where the reveal is located at various locations along the electrode.

The embodiment presented in FIG. 11 presents electrode array 102 wherein the electrodes 108 are of equal length but each has a reveal 116 that is disposed at various locations along the length of electrode 108 such that contact with the living tissue occurs with different tissue bundles, for example. While not illustrated, it is envisioned by the inventors that the spacing between electrodes 108 may be variable and need not be equidistant from each other.

Figure 12:
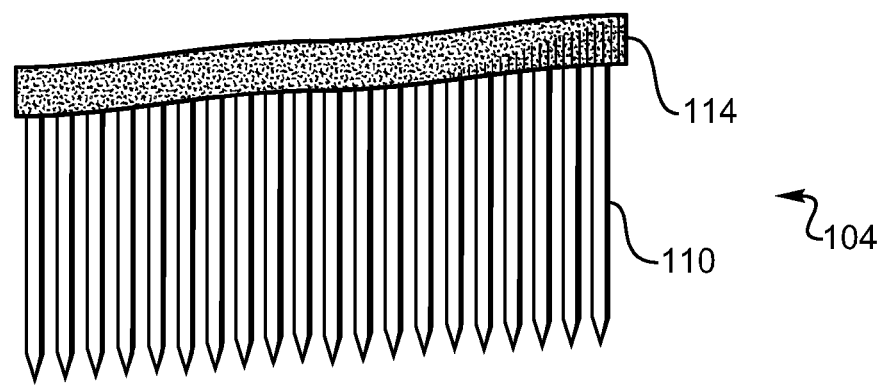
FIG. 12 is a side view of an embodiment of an electrode array on a non-flat irregular substrate where the electrode length varies.

The embodiment of FIG. 12 presents an electrode array 104 wherein the electrodes 110, which are bonded to non-flat, irregular substrate 114, have irregular lengths. The reveals, not illustrated, may be arranged in a multitude of arrangements, as described for FIG. 11.

The alternative embodiment of FIG. 13 presents the electrodes 4 inserted through the substrate 14 from the bottom surface 126. The contact surface 122 of terminal 120 provides a connecting surface to the other electrical circuits. In this configuration, FIG. 13, the braze surface 74 is concealed from the living tissue environment.

FIG. 14 presents an embodiment that is similar to that of FIG. 13, except that presenting contact surface 120 is on brazing head 24, which results in more readily formed electrodes 4.

FIG. 15 is more readily formed that the electrode of FIG. 13 or 14 and contact surface 122 is formed on shaft 22.

The substrate 14, FIG. 16, contains a number of feedthrough holes 20 which correspond to the number and configuration of electrodes 4 when they are arranged in the electrode array 6. The electrodes 4 then terminate with feedthrough 26 which, in the embodiment presented in FIG. 16, enter feedthrough hole 20 from the bottom surface 126 of substrate 14 until brazing head 24 contacts braze preform 16, which in turn contacts substrate 14.

Although the invention has been described and illustrated in detail, it is to be clearly understood that the same is by way of illustration and example only and is not to be taken by way of limitation, the spirit and scope of this invention being limited only by the terms of the appended claims.

What is claimed is:

1. A method for making an implantable hermetically sealed electrically conductive electrode array suitable for neuron interface and cortical implants that is comprised of a substrate, a braze perform, and electrically conductive electrodes, comprising the steps of:
    selecting a substrate material comprised of ceramics selected from the group consisting of: zirconia, stabilized-zirconia, partially-stabilized zirconia, tetragonal zirconia polycrystal, magnesia-stabilized zirconia, ceria-stabilized zirconia, yttria-stabilized zirconia, calcia-stabilized zirconia, silicon, sapphire, alumina, or germanium;
    obtaining said substrate with a plurality of feedthroughs;
    placing a braze preform having a predetermined melting point, said preform comprised of tabs configured to locate holes, said holes sized to accept an electrically conductive electrode, and voids that are defined by said tabs on said substrate;
    selecting titanium nickel layered laminates as said braze preform;
    selecting said electrically conductive electrode from titanium, titanium alloy, platinum, platinum alloy, activated iridium, platinum-iridium alloy, conductive polymer, or carbon material for use in connection with the body
    inserting said electrically conductive electrode into each of said plurality of feedthroughs; and
    forming said implantable hermetically sealed electrically electrode array that is suitable for neuron interface and cortical implants by bonding said electrically conductive electrode to each of said plurality of feedthroughs by thermal brazing at a known temperature above the melting point of said braze preform, wherein said tab is drawn into the feedthrough.

2. The method of claim 1 for making an electrically conductive electrode array further comprising the step of selecting tabs having a maximum width of 0.1 inch, a maximum length of 0.2 inch, and a maximum thickness of 0.01 inch.

3. The method of claim 1 for making an electrically conductive electrode array further comprising the step of bonding at said temperature of between 25 and 300 degrees Centigrade above the braze preform melting point.

* * * * *